US009161905B2

(12) United States Patent
Korb et al.

(10) Patent No.: US 9,161,905 B2
(45) Date of Patent: Oct. 20, 2015

(54) DRY EYE TREATMENT

(75) Inventors: Donald R. Korb, Boston, MA (US);
Chris J. Brancewicz, Potsdam, NY (US)

(73) Assignee: Ocular Research of Boston, Inc., Boston, MA (US)

( * ) Notice: Subject to any disclaimer, the term of this patent is extended or adjusted under 35 U.S.C. 154(b) by 2470 days.

(21) Appl. No.: 11/034,527

(22) Filed: Jan. 12, 2005

(65) Prior Publication Data
US 2006/0153885 A1 Jul. 13, 2006

(51) Int. Cl.
*A61K 9/00* (2006.01)
*A61K 9/107* (2006.01)

(52) U.S. Cl.
CPC .............. *A61K 9/0048* (2013.01); *A61K 9/107* (2013.01)

(58) Field of Classification Search
CPC ............................ A61K 9/0048; A61K 9/107
See application file for complete search history.

(56) References Cited

U.S. PATENT DOCUMENTS

| 4,421,748 | A | 12/1983 | Trager et al. |
| 4,522,803 | A | 6/1985 | Lenk et al. |
| 4,649,047 | A | 3/1987 | Kaswan |
| 4,677,099 | A | 6/1987 | Shinitzky et al. |
| 4,804,539 | A | 2/1989 | Guo et al. |
| 4,818,537 | A | 4/1989 | Guo |
| 4,839,175 | A | 6/1989 | Guo et al. |
| 4,839,342 | A | 6/1989 | Kaswan |
| 4,866,049 | A | 9/1989 | Maumenee et al. |
| 4,908,154 | A | 3/1990 | Cook et al. |
| 4,914,088 | A | 4/1990 | Glonek et al. |
| 4,923,699 | A | 5/1990 | Kaufman |
| 4,923,700 | A | 5/1990 | Kaufman |
| 4,938,965 | A | 7/1990 | Shek et al. |
| 4,966,773 | A | 10/1990 | Gressel et al. |
| 5,041,434 | A | 8/1991 | Lubkin |
| 5,185,372 | A | 2/1993 | Ushio et al. |
| 5,252,246 | A * | 10/1993 | Ding et al. .................... 510/137 |
| 5,294,607 | A * | 3/1994 | Glonek et al. ................... 514/76 |
| 6,436,429 | B1 * | 8/2002 | Peyman ......................... 424/435 |
| 2003/0165545 | A1 | 9/2003 | Huth et al. |
| 2005/0059583 | A1 | 3/2005 | Acheampong et al. |

FOREIGN PATENT DOCUMENTS

| AU | 16149/76 | 1/1978 |
| EP | 0 241 376 | 10/1987 |
| EP | 0 391 369 | 4/1990 |

OTHER PUBLICATIONS

Hardberger, Hanna and Boyd, "Effects of Drug Vehicles on Ocular Contact Time," Arch. Ophthalmol., vol. 93, Jan. 1975.

* cited by examiner

*Primary Examiner* — Sean Basquill
(74) *Attorney, Agent, or Firm* — Slater & Matsil, L.L.P.

(57) ABSTRACT

This invention relates to an emulsion composition for the formation of an artificial tear film over the ocular surface of the eye capable of providing mechanical lubrication for the ocular surface while reducing evaporation of fluid therefrom. The emulsion is desirably in the form of a meta stable emulsion and is characterized by the use of a surfactant comprising a combination of a primary and secondary surfactant where the primary surfactant permits formation of the emulsion and the secondary surfactant permits autoclaving of the surfactant. The invention also includes a method for the formation of such an emulsion.

24 Claims, No Drawings

DRY EYE TREATMENT

BACKGROUND OF THE INVENTION

1. Introduction

This invention relates to an emulsion composition for the formation of an artificial tear film over the ocular surface of the eye capable of providing mechanical lubrication while reducing evaporation of fluid. The composition is also useful for delivering medication to the ocular surface and for treating individuals wearing ocular prostheses such as contact lenses as the composition wets and provides lubrication for both the ocular surface and the surface of the prosthesis. More particularly, the invention relates to emulsion compositions capable of augmenting and maintaining a stable tear film over the ocular surface and/or delivering a medication to said surface without causing substantial blurring of vision nor discomfort. The emulsion is desirably in the form of a meta stable emulsion and is characterized by the use of a surfactant combination suitable for formation such an emulsion and maintaining the integrity of the emulsion during high temperature autoclaving.

2. Description of the Prior Art

It is known in the art that an aqueous tear film extends over the ocular surface and maintains the ocular surface moist and lubricated. It is also known that dehydration of moisture from the eye may result in discomfort. Further, it is known that compositions are available in the market intended for dry eye treatment. Commercially available compositions are primarily aqueous materials that supplement the tear film by adding a film of a water-soluble polymer over the surface of the eye. This film is short lived and provides limited relief.

The feeling of discomfort resulting from a dry eye condition may include ocular dryness, grittiness, burning, soreness or scratching, dependent upon the subject and the condition of the subject. Proposed causes for dry eye, treatment, and symptoms are described in a compendium of papers edited by Holly, The Preocular Tear Film in Health, Disease, and Contact Lens Wear, The Dry Eye Institute, Lubbock, Tex. 1986; edited by David A. Sullivan, Lacrimal Gland, Tear Film, and Dry Eye Syndromes, 1994, Plenum Press, New York; edited by David A. Sullivan et. al, Lacrimal Gland, Tear Film, and Dry Eye Syndromes 2, 1998, Plenum Press, New York; edited by David A. Sullivan et. al, Lacrimal Gland, Tear Film, and Dry Eye Syndromes 3, Part A and B, 2002, Kluwer Academic/Plenum Publishers, New York incorporated herein by reference for their teachings of the dry eye condition and the treatment thereof.

The most common treatment for dry eye involves temporary alleviation of dry eye symptoms by topical application of a tear substitute that adds a large volume of liquid to the anterior surface of the eye and related adnexa. Typical commercially available tear substitute compositions comprise water-soluble polymer solutions. Examples of such solutions include saline solutions of polyvinyl alcohol, hydroxypropylmethyl cellulose, or carboxymethyl cellulose. U.S. Pat. No. 4,421,748 teaches an artificial tear composition comprising an aqueous hypotonic solution of lecithin and a viscosity-adjusting agent such as a solution of a soluble cellulose.

Methods used to quantify the effectiveness of tear substitutes for dry eye treatment solutions have not been standardized, and many methods used to quantify the results obtained using such tear substitute compositions are often inaccurate. For this reason, it is known that reported relief of dry eye symptoms using known tear substitutes varies considerably from subject to subject, and regardless of the method used to quantify relief using a tear substitute, relief often does not exceed several minutes.

The symptoms associated with dry eye are often exacerbated with subjects using ocular prostheses such as contact lenses. In some cases, contact lens intolerance is caused in part, or in total, by the condition of dry eye and its symptoms. Further, the rate of evaporation from the eye is accelerated by the nature of the contact lens surface and the physical presence of the contact lens results in meniscii formation with additional physical and evaporative effects, even with subjects having an adequate tear film. For many subjects, contact lens intolerance is not overcome by topical application of tear substitutes. Therefore, there is a need for improved compositions and processes for treatment of the dry eye condition and for improving tolerance to ocular prostheses.

Improved compositions for dry eye treatment are disclosed in U.S. Pat. Nos. 4,914,088; 5,278,151; 5,294,607; 5,578,586, each incorporated herein by reference for its teaching of how to form an oil film over the surface of the eye including compositions used therefor. U.S. Pat. No. 4,914,088 teaches the use of certain charged phospholipids for the treatment of dry eye symptoms. The addition of a charged phospholipid to the eye is believed to assist in replicating the tear film that would naturally occur in the eye. In accordance with the patent, the phospholipid composition, preferably in the form of an aqueous emulsion, is topically applied to the eye where it is believed to disperse over the ocular surface and form a film that replicates a lipid layer that would be formed by the spreading of a naturally occurring lipid secreted principally from the meibomian glands during blinking. Because the phospholipid, when applied to the eye, in one embodiment, carries a net negative charge, it is believed that aligned molecules repel each other preventing complex aggregate formation thereby resulting in a stable phospholipid film. The patent theorizes that the film formed from the charged phospholipid assists in the formation of a barrier film reducing evaporation of the aqueous layer, thereby preserving the tear film. It is also now theorized that the phospholipid also functioned as a surfactant maintaining the emulsion stable.

The above referenced U.S. Pat. Nos. 5,278,151; 5,294,607; and 5,578,586 disclose further improvements in dry eye treatment. In accordance with the disclosure of said patents, the dry eye treatment composition of U.S. Pat. No. 4,914,088 is improved by the addition of an oil to the eye treatment composition, preferably a non-polar oil. The oil is added to improve the performance of a dry eye treatment composition by increasing the longevity of the tear film formed on the eye as a consequence of the formation of an oil film over the ocular surface that functions as an evaporation barrier—i.e, by providing and/or thickening the dehydration barrier (the oil layer) on the outer surface of the tear film. Thus, the oil increases the efficacy of the dry eye treatment solution and reduces performance variability from subject to subject.

A preferred embodiment disclosed in the above referenced patents is a dry eye treatment composition comprising a meta stable oil in water emulsion where the water phase includes the charged phospholipid believed to function both as an emulsifier and as a surfactant that assists in spreading of the oil over the eye to form a non-blurring film bonding of the oil to the ocular surface. Preferably, the oil phase comprises a non-polar oil. In accordance with this preferred embodiment, the emulsion is desirably "meta" stable so that when the emulsion is applied to the eye, it will rapidly break and spread over the ocular surface when it first comes into contact with the ocular surface, all as explained in the aforesaid patents.

The meta stable emulsions of the foregoing patents are formulated whereby the total amount of oil added to the eye preferably does not exceed 25 ul, more preferably varies between about 1 and 10 ul and most preferably varies between about 1 and 5 ul. If the amount of oil added to the eye is in excess of 25 ul, the oil layer on the surface of the eye may be of excessive thickness resulting in formation of oil globules on the surface of the eye. These globules are likely to result in prolonged blurring. To achieve control of the amount of oil added to the eye, the concentration limits of the oil in the emulsion are controlled within reasonable limits. An emulsion containing the oil in a concentration of at least 0.1 percent by weight of the total composition provides some benefits, a preferred concentration is at least 1.0 percent of the weight of the treatment composition, and the most preferred oil content varies between about 2.5 and 12.5 percent by weight of the emulsion.

Though the use of an oil in water meta stable emulsion having a negatively charged phospholipid as a surfactant provides excellent clinical results for dry eye treatment, there are certain disadvantages associated with their use. For example, the phospholipid component is costly when manufactured to the requirements and tolerances required for use on the eye. In addition, the storage of the phospholipids requires special conditions. Further, the lack of a long history relating to the use of a phospholipid on the eye could raise questions regarding safety and might create possible concerns by regulatory agencies that might require lengthy and costly clinical trials for approval. A further problem involves possible reluctance of companies marketing eye treatment products to deviate from the use of those ingredients having a long history of uneventful use in existing, commercially available treatment products.

For the foregoing reasons, it is desirable to find one or more surfactants that may be substituted for the charged phospholipids used to form a meta stable oil in water emulsion as disclosed in the aforesaid patents. Though it might appear that simple trial and error could be used to find a suitable surfactant, the task of finding a substitute surfactant is difficult. For example, the replacement surfactant must be acceptable for human use. Many available surfactants are not approved for use on the ocular surface. The replacement surfactant must not cause discomfort to the patient when used in a concentration adequate to form the desired emulsion. Many surfactants may not be added to the eye in suitable concentration without causing stinging. A physiological pH of between about 7.0 and 7.8 is required for application to the ocular surface. Many surfactants function as surfactants within a prescribed range of pH, both above and below pH 7. The desired emulsion for treatment of dry eye is preferably meta stable enabling it to rapidly break when applied to the eye. Therefore, the replacement surfactant must enable formation of an emulsion that is stable in manufacture and storage and meta stable and capable of breaking when applied to the ocular surface. The replacement surfactant must be capable of forming an emulsion containing oil in an acceptable concentration as described above to avoid prolonged blurring following application. Finally, the emulsion formed must be sufficiently robust to withstand sterilization at elevated temperatures without breaking but sufficiently unstable so as to break when applied to the eye. It has been found that many replacement surfactants capable of forming a stable emulsion are incapable of maintaining stability of the emulsion during autoclaving at that temperature required for sterilization if used in a concentration suitable for addition to the eye without causing stinging, or in the alternative, if sufficient to withstand autoclaving, may be so robust that they will not break when applied to the eye.

SUMMARY OF THE INVENTION

In accordance with the subject invention, it has been found that a preferred meta stable oil in water emulsion suitable for application to the ocular surface for treatment of the eye may be formed using a combination of surfactants as emulsifiers where one surfactant is a physiologically acceptable surfactant capable of forming the desired meta stable emulsion at physiological pH, hereafter the "primary surfactant", and an additional surfactant, used in combination with the primary surfactant, is a physiologically acceptable surfactant capable of maintaining the emulsion stable during autoclaving at temperatures in excess of 75° C. or higher without preventing the emulsion from breaking when applied to the eye, hereafter the "secondary surfactant".

The preferred primary surfactant comprises any one or more physiologically acceptable surfactants capable of forming a meta stable oil in water emulsion at pH between about 7.0 and 7.8 without causing discomfort to the patient when used in a concentration adequate to form the desired emulsion having an oil phase in a concentration of from 1.0 percent by weight up to that amount below that which would causes blurring. The term "meta stable emulsion" means one that is stable in storage but breaks rapidly when instilled onto the ocular surface as described in the above referenced U.S. Pat. Nos. 5,278,151; 5,294,607; 5,578,586. The primary surfactant may be identified by routine experimentation using procedures described below. Surprisingly, other than the phospholipids, the subject of the above referenced patents, no single surfactant has been found capable of use as a sole surfactant to form a meta stable emulsion meeting the guidelines set forth herein though it should be understood that such an emulsion might be formed using a single surfactant in high a concentration whereby the patient is likely to experience stinging when the emulsion is added to the eye.

The preferred secondary surfactant is one or more physiologically acceptable surfactants that is used in conjunction with the primary surfactant which does not alter the meta stable form of the emulsion and does not cause discomfort to the patient at efficacious concentration, while stabilizing the emulsion by preventing decomposition at the elevated temperatures required for autoclaving, typically at temperatures in excess of 75° C. and desirably at temperatures at or in excess of 100° C. Though not mandatory for all secondary surfactants, as a guideline only, the secondary surfactant desirably has a relatively long chain with a minimum of 6 hydrophilic groups and an HLB of 9 or more, and preferably an HLB ranging between 12 and 20, and a lipophilic group that is small in relation to the hydrophilic group and preferably, the same or similar in structure to the lipophillic group of the primary surfactant.

From the literature, it would be expected that one skilled in the art would select a surfactant combination having an arithmetic mean HLB of between about 8 and 14 and more typically, between about 10 and 12 for formation of an oil in water emulsion of the type described herein. The arithmetic mean is determined based upon the HLB of the individual surfactants selected and the concentration of each surfactant used. Unexpectedly, an arithmetic HLB of between 8 and 14 is not required for purposes of the present invention as will be demonstrated below.

DESCRIPTION OF THE PREFERRED EMBODIMENTS

The treatment composition of the invention is an oil in water emulsion having an aqueous phase, an oil phase, and a surfactant combination used for the dual purpose of stabilizing the emulsion and spreading the emulsion over the ocular surface following its application to the eye. The surfactant combination comprises a primary surfactant and secondary surfactant and is one that enables formation of an emulsion that is stable in manufacture and during storage, but desirably meta stable when applied to the ocular surface—i.e., one that rapidly differentiates when applied to the eye whereby a non blurring film of oil is rapidly formed over the ocular surface. A stable emulsion during manufacture and storage is one that may separate into separate phases during standing, but can be reconstituted by simple shaking. An unstable emulsion is one that breaks typically forming an oil film or slick that cannot be eliminated by simple shaking.

A meta stable emulsion during use is desirable for purposes of this invention. Though useable for alleviation of dry eye symptoms, a stable emulsion, as opposed to a meta stable emulsion, will not differentiate rapidly when applied to the ocular surface. This is undesirable for the following reasons. An emulsion is typically optically opaque due to the presence of two distinct phases. Therefore, an opaque emulsion over the surface of the eye is likely to cause blurring. The duration of blur is dependent upon the time required for the emulsion to differentiate and form separate layers replicating a tear film. In addition, the emulsion is most easily added to the eye as a standard drop from an eyedropper. The eye is capable of holding a limited volume of fluid—a volume that is less than 25 µl. A volume of 25 µl is substantially less than the volume of a standard drop. Therefore, if the emulsion is stable and fails to differentiate rapidly following application to the eye, excess emulsion will be discharged from the eye during blinking. Discharge of the emulsion from the eye will result in discharge of efficacious components of the treatment solution from the eye before a long lasting tear film can be formed. For this reason, efficacious components may not be available in sufficient quantity to form the desired tear film. Consequently, though a stable emulsion might alleviate the symptoms of dry eye for a limited period of time, it is a lesser preferred embodiment of the invention.

A meta stable emulsion, as the term is used herein, is one that is either stable in storage, or differentiated into two separate layers, but is readily reconstituted by simple shaking prior to use. When a meta stable emulsion is added to the eye as a standard drop, it quickly differentiates permitting rapid formation of an oil film over the corneal surface without excessive oil discharge by blinking. Preferably, the emulsion will differentiate within about 5 blinks following application to the eye, more preferably in a time of less than about 30 seconds. Blurring may occur during the time required to move the bulk of the excess liquid to the canthi and discharge the same from the eye. During and following differentiation of the emulsion, the formation of the oil film is assisted by use of the surfactant combination which serves to help form the emulsion and facilitate the spread of the oil over the surface of the eye as the emulsion breaks. Consequently a meta stable emulsion is the preferred embodiment of this invention.

The surfactant combination used to form a meta stable emulsion must be carefully selected and must meet the following criteria:

a. the surfactant combination must enable formation of an emulsion having long term stability, especially when exposed to the high temperatures of autoclaving needed to sterilize the formulation during manufacture, while permitting rapid phase differentiation when applied to the surface of the eye;

b. each component of the surfactant combination must be compatible with other components of the emulsion composition and permit formation of the emulsion at the physiological pH of between about 6.5 and 7.8 and preferably, at pH of between 7.2 and 7.5; and c. each component of the surfactant combination must be pharmaceutically acceptable for use on the eye and must be compatible with the eye—i.e., each should be nontoxic and should not cause discomfort such as stinging in the concentrations used.

As described above, the surfactants used to form the emulsions of the invention comprise a combination of a primary surfactant and a secondary surfactant.

The primary surfactant is any one or more pharmaceutically acceptable surfactants that meets the above criteria and desirably forms a meta stable emulsion by itself or in combination with the secondary surfactant, but differs in chemical structure from the secondary surfactant. The literature is replete with thousands of surfactants having a variety of chemical structures described as useful for the formation and stabilization of an oil in water emulsion. To provide an exhaustive list of representative surfactants capable of functioning as a primary surfactant for purposes of the subject invention would be laborious and would omit many useful candidate materials. Therefore, in addition to the representative examples given below, a procedure is given intended to enable one skilled in the art to determine if a given surfactant may be used as a primary surfactant in accordance with the preferred embodiment of the subject invention. This procedure involves the following steps:

a. select a surfactant approved for use on the ocular surface within a useful concentration range as given below;

b. from the literature or by testing, determine if the surfactant is capable of forming an emulsion with the oil and water components at physiological pH;

c. prepare an emulsion having the concentration of emulsion components given below and determine if the emulsion is stable during storage, a minimum of three months under normal storage conditions, or capable of being reconstituted by simple shaking; and d. apply the emulsion to the ocular surface and determine if the emulsion breaks on the ocular surface within a minute or less, preferably in less than 30 seconds or 5 blinks.

Representative examples of primary surfactants meeting the criteria given above include ionic and non-ionic surfactants but non-ionic surfactants are preferred as they are less prone to cause stinging when applied to the eye. Specific examples of the nonionic surfactant include alkyl ethers such as polyoxyethylene octyl ether, polyoxyethylene lauryl ether, polyoxyethylene stearyl ether and polyoxyethylene oleyl ether; alkyl phenyl ethers such as polyoxyethylene octylphenyl ether and polyoxyethylene nonylphenyl ether; alkylesters such as polyoxyethylene laurate, polyoxyethylene stearate and polyoxyethylene oleate; alkylamines such as polyoxyethylene laurylamino ether, polyoxyethylene stearylamino ether, polyoxyethylene oleylamino ether, polyoxyethylene soybean aminoether and polyoxyethylene beef tallow aminoether; alkylamides such as polyoxyethylene lauric amide, polyoxyethylene stearic amide and polyoxyethyleneoleic amide; vegetable oil ethers such as polyoxyethylene castor oil ether and polyoxyethylene rapeseed oil ether; alkanol amides such as lauric acid diethanol amide, stearic acid diethanol amide and oleic acid diethanol amide; and sorbitan ester ethers such as polyoxyethylene sorbitan monolaurate, polyoxyethylene sorbitan monopalmitate, polyoxyethylene sorbitan monostearate and polyoxyethylene sorbitan monooleate. Of the above, polyoxyethylene stearates are preferred. Additional suitable surfactants can be found by reference to a standard text on surfactants such as those described in Ash and Ash, Encyclopedia of Surfactants, Chemical Publishing Company, New York, 1985; McCutcheon's Emulsifiers and Detergents, North American Edition, McCutcheon Publishing Company, Glen Rock, N.J., 2000; and Remington: The Science and Practice of Pharmacy, Nineteenth Edition, Vol. 1 at p. 251 coupled with the use of the procedures set forth above.

The secondary surfactant is one or more surfactants meeting the above criteria and in addition, enables the emulsion to withstand autoclaving without significant degradation of the emulsion. The secondary surfactant desirably has a relatively small lipophilic group and a long chain hydrophilic group with a minimum of 6 repeating hydrophilic groups. More preferably, the secondary surfactant has an HLB of 9 or more, and most preferably, an HLB ranging between 12 and 20, a hydrophilic group of at least 9 repeating hydrophilic groups, most preferably at least 9 ethylene oxide groups or isopropyl oxide groups, and a relatively small lipophilic group that is the same or similar in structure to the lipophilic group of the primary surfactant. Exemplary nonionic surfactants include, but are not limited to the Octoxynol-n series of the formula $C_8H_{17}C_6H_4(OCH_2CH_2)_nOH$ where n is between 5 and 70 and preferably between 30 and 50, the nonoxynol-n series of the formula $C_9H_{19}C_6H_4(OCH_2CH_2)_pOH$ where p is between 5 and 40 and preferably between 15 and 30, and polyoxyethylene $C_{12-22}$ alkyl ethers such as polyoxyethylene lauryl ether, polyoxyethylene cetyl ether, polyoxyethylene stearyl ether or polyoxyethylene oleyl ether. Most preferred secondary surfactants are the Octoxynol series of surfactants having between 30 and 50 ethylene oxide groups. Numerous other surfactants having an HLB value of greater than about 9 and meeting the above criteria are listed in Ash and Ash, McCutcheons, and Remington, supra.

The concentration of the surfactant combination used to form the emulsion may vary within wide limits. A treatment composition containing the surfactant combination in an amount as low as 0.01 weight percent of the total composition provides some benefit. A concentration of surfactant combination varying between 0.05 to 5.0 percent of the total composition is a clinically practical concentration range for purposes of the invention provided that the surfactant does not cause patient discomfort when used at the higher concentrations. Most preferably, the concentration of the combination varies between about 0.25 and 2.5 percent by weight of the total composition. It should be understood that with many surfactants, as concentration increases, the likelihood of physical discomfort—i.e., stinging, of the emulsion on the eye increases. Thus, if significant stinging occurs when the emulsion is applied to the ocular surface, it is likely that the concentration of surfactant is too high.

The ratio of the primary surfactant to the secondary surfactant may vary within relatively broad limits—for example, between 0.2 to 1.0 to 1.0 to 0.2 primary to secondary surfactant. A more preferred range varies between 0.5 to 1.0 and 1.0 to 0.5. Most preferably, the primary surfactant is used in slightly larger concentration than the secondary surfactant and the most preferred ratio varies between 1.0 to about 0.75.

The emulsions of the invention comprise an oil in water emulsion. The oil used to form the emulsion may be derived from animals, plants, nuts, petroleum, etc. Those derived from animals, plant seeds, and nuts are similar to fats and are primarily glycerides or fatty acids and consequently, contain a significant number of acid and/or ester groups rendering the same polar and lesser preferred for purposes of the invention. Alternatively, oils derived from petroleum are usually aliphatic or aromatic hydrocarbons that are essentially free of polar substitution and therefore suitable for purposes of the present invention provided the oil is refined so as to be compatible with human tissue such as the ocular surface. Preferably, the oil is a linear hydrocarbon oil having from 10 to 50 carbon atoms and more preferably, the oil is a saturated n-alkane or isoalkane hydrocarbon having from 14 to 26 carbon atoms. Unsaturated alkene hydrocarbons may be used but are less chemically stable. Aromatic oils are lesser preferred because it is known that aromatic compounds are for the most part unsuitable for application to the ocular surface. Mineral oil is the most preferred oil for purposes of this invention.

The oil component within the emulsion may vary within reasonable limits provided the amount of oil retained on the eye following its application to the eye is within controlled volumes and does not exceed 25 ul, more preferably varies between about 1 and 10 ul and most preferably varies between about 1 and 5 ul. If the amount of oil added to the eye is in excess of 25 ul, the oil layer on the surface of the eye may be of excessive thickness and resulting in prolonged blurring. A treatment composition containing the oil in a concentration of at least 0.1 percent by weight of the total composition provides some benefits. A preferred concentration for the oil is at least 1.0 percent of the weight of the treatment composition. Preferably, the oil content of the treatment solution varies between about 2.5 and 12.5 percent by weight of the composition.

Other additives may be present in the treatment composition. Such materials include minor amounts of neutral lipids and oils such as one or more triglycerides, cholesterol esters, the natural waxes and cholesterol; high molecular weight isoprenoids; stabilizers, additional surfactants; preservatives; pH adjusters to provide a composition preferably having a pH between about 6.5 and 7.8 and most preferably, between about 7.2 and 7.5; salt, glycerol or sugar in sufficient concentration to form an isotonic or mildly hypotonic composition; etc., all as would be obvious to those skilled in the art.

Another useful class of additives comprises medications. As a consequence of the long term stability of the oil film formed over the surface of the eye using the emulsion compositions of the invention, prolonged and improved delivery of the medication to the eye results due to increased contact time of the medication on the eye. Medications suitable for delivery to the eye using the film forming compositions of the invention are those soluble in either the aqueous or oil phase of the composition though it is preferable that the medication be soluble in the oil phase. Illustrative medications include antibiotics, antiviral agents, anti-inflammatory agents and antiglaucoma agents such as illustrated in part in published European Patent Application No. 0 092 453 published Oct. 26, 1983, sections 5.3.1 and 5.3.2, incorporated herein by reference.

Any additional additives added to the emulsion are added prior to formation of the emulsion using simple mixing techniques. The concentration of the additive is dependent upon the specific additive, and preferably, total additive content in addition to the surfactant and the oil are at a maximum concentration level whereby the total weight of the organics in the oil phase does not exceed 15 percent of the total weight of the emulsion.

In accordance with the invention, the emulsions may be made in accordance with standard procedures. Desirably, a commercial homogenizer is used to form the emulsion as equipment of this nature enhances the stability of the emulsion during transportation and storage. The use of commercial homogenizers for the formation of emulsions is within the skill of the art.

The emulsions of the invention are also desirably used with subjects requiring ocular prostheses. In this instance, the treatment composition enhances the tear film layer and lubricates the boundary between the prosthesis and the ocular surface. When used with an ocular prosthesis, the treatment composition may be applied to the inner or both the inner and outer surfaces of the prostheses prior to insertion of the same into the eye. Regardless of how added, the amount available to form the oil layer should be within the limits set forth above.

The invention will be better understood by reference to the examples that follow. In the examples, the thickness of the lipid layer of a tear film formed over the ocular surface is evaluated by projecting a light source onto the ocular surface while viewing the reflected images from the light source on a video screen. The light source and its location is one that illuminates a surface area on the ocular surface of approximately 10 mm². Interference patterns are formed, the color(s) of which are indicative of the thickness of the oil layer. The color of the waves is correlated with a protocol of known film thickness. In this way, the tear film can be evaluated over a period of real time and rated in accordance with the following scale:

| Rating | Film Characteristics | Quality |
|---|---|---|
| A | Colored waves - particularly greens and blues. Waves extend from lower to above the lower pupillary border. Film thickness is excess of 170 nm. | Excellent |
| B | Colored waves - reds, browns, yellows, but no blues. Waves extend from lower lid to above the pupillary border. Film thickness of approximately 90 nm. | Good |
| C | Colored waves - only yellow is present. Waves extend form lower lid to lower pupillary border. Film thickness of approximately 90 nm. | Good |
| D | Waves visible but no color present or no color other than grayish white. Waves extend from lower lid to lower pupillary border. Film thickness of less than 90 nm. | Fair |
| E | No waves and no color. An absence of any observable tear film movement. Film thickness of less than 70 nm. | Poor |

Further details pertaining to experimental procedure can be found in the above referenced U.S. Pat. Nos. 5,278,151; 5,294,607; and 5,578,586.

The data presented in the examples was obtained using individuals with baseline lipid layers of C rating or less. The data illustrates the resultant change in lipid layer characteristics from the baseline finding to the finding for lipid characteristics after the application of a standard eye drop of the test formulation to the eye. A desirable result is for improvement in lipid layer characteristics, evidenced by an increase in the alphabetical grade, with A being the most desirable, and F being the least desirable. The evaluations were performed 5 minutes after the instillation of the test formulations.

The first two examples illustrate that emulsions may be formed using surfactants having properties and HLBs suggesting suitability for formation of stable oil in water emulsions, but illustrate that the emulsions so formed are unstable at autoclaving temperatures and therefore unsuitable for dry eye treatment. Example 3 illustrates that a surfactant that might be suitable for formation of an emulsion having properties meeting the objectives of this invention is unsuitable as it causes discomfort to the patient when added to the eye. Examples 4 and 5 illustrate that primary surfactants unsuitable for formation of a dry eye emulsion can be made functional when used in combination with the secondary surfactants of the invention regardless of the arithmetic HLB.

EXAMPLE 1

This example illustrates that various surfactant combinations may be used that meet certain of the guidelines set forth above, especially those relating to HLB, but still fail to provide a meta stable emulsion able to withstand the elevated temperatures required for sterilization of the formulation.

A mixture of Myrj-52, a polyoxyethylene (40) stearate, and glycerol monostearate (GMS), were used as primary surfactants to form a dry eye treatment emulsion with mineral oil as the oil phase. Myrj-52 has a high HLB value (15-16.9) and is water-soluble. Glycerol monostearate (GMS NF) has a low HLB value (3-5) and is therefore oil soluble suggesting that the combination should form a suitable oil in water emulsion. These surfactants have an identical lipophilic group (stearate) but different hydrophilic groups, and thus will have different physical behavior in terms of partitioning into the oil or water phases as suggested by the difference in the HLB value of the two surfactants.

This combination of surfactants was evaluated by formation of 11 emulsions utilizing 5.5% (±0.3%) of Drakeol-35, a commercially available mineral oil at two different total surfactant concentrations—0.15% and 0.30%. The non-polar oil phase of Drakeol-35 mineral oil and the aqueous phase of 0.67% NaCl and 0.05% of anhydrous $Na_2HPO_4$ were common to all 11 of these formulations; the pH was adjusted with diluted HCl as required. The relative concentration of the two individual surfactants was varied to evaluate the effect of the average HLB on emulsion quality as shown in Table 1. Emulsification of the 11 formulations was performed using a commercial homogenizer (PRO250) from Proscientific, Inc., with a ¾ horsepower motor which drove a 30 mm rotor-stator generator, by combining all of the reactants into one vessel and raising the temperature to approximately 90° C. Table 1 provides the formulations and the compositions (in grams) for the 11 test formulations utilizing the Myrj-52 and GMS primary surfactant systems.

TABLE 1

| gm Myrj-52 | gm GMS | gm Drakeol 35 | Surfactant Content |
|---|---|---|---|
| 0.094 | 0.065 | 5.700 | 0.15% |
| 0.102 | 0.054 | 5.334 | 0.15% |
| 0.112 | 0.042 | 5.508 | 0.15% |
| 0.127 | 0.037 | 5.404 | 0.15% |
| 0.130 | 0.030 | 5.284 | 0.15% |
| 0.139 | 0.020 | 5.284 | 0.15% |
| 0.298 | 0.017 | 5.309 | 0.30% |
| 0.279 | 0.042 | 5.300 | 0.30% |
| 0.258 | 0.065 | 5.283 | 0.30% |
| 0.233 | 0.091 | 5.308 | 0.31% |
| 0.207 | 0.108 | 5.303 | 0.30% |

Footnotes
1. Myrj-52 is polyoxyethylene (40) stearate
2. Glyceryl monostearate (GMS) is the glycerol ester of stearic acid
3. Drakeol refers to a series of NF mineral oils available from Penreco Co. of Butler, PA. The numeral following the letters represents the average molecular weight of the oil, and is an indication of the viscosity of the fluid.

Results

The formulations of Table 1 produced emulsions which all met the first criterion of separation when at rest for several minutes. They also appeared to meet the second criterion of the emulsion returning to its original dispersed form after simple agitation. However, after periods of 60 minutes to 1 day, some of the oil phase in the formulations with the higher HLB values evidenced significant oil breakout, where the individual oil droplets were broken, resulting in the formation of an oil film on the surface.

The formulations with the lower HLB values provided emulsions that did not evidence the oil film after similar periods of time. However, when agitated with mechanical shaking to simulate transportation effects, the oil film was visible on the surface within a time period that precluded a commercially viable product.

In general, an increasing value of the calculated HLB produced poorer quality emulsions upon standing or upon agitation. However, no formulation in Table 1 was found to be adequate because of the degradation of the individual oil droplets and the subsequent formation of a surface oil layer. Further, microscopic studies and photographs of these formulae taken before and after both autoclaving and shaking demonstrated that the oil droplets were degraded either by being subjected to autoclaving at 121° C. or by shaking on the Platform Rocker Shaker by Vari-Mix for less than one day.

The above example illustrates that for the materials of this example, HLB values alone proved to be an unreliable parameter of complex formulation issues in the development of the intended dry eye treatment composition. While HLB values are generally useful as a formulation development guide, it was obvious that further considerations are required for the development of a dry eye treatment composition suitable for purposes of this invention.

Resolution of the above described problem would likely require significantly higher surfactant concentrations but it was known that increasing the concentration of Myrj-52% would result in ocular discomfort—i.e. significant stinging. For this reason, the formulation was not evaluated clinically.

EXAMPLE 2

Polysorbate-80 (trade name Tween-80), a stearyl ether of a polysorbate, was evaluated as a sole primary surfactant for forming a dry eye treatment emulsion utilizing a total concentration of 7.0% of a mineral oil mixture of Draekol-15 and Draekol-35. In this study, Polysorbate-80 concentrations of 0.2%, 1.0%, and 1.5% were utilized in the base formula as displayed in Table 2 as formulae C1 through C6. These formulations were prepared with and without disodium EDTA. Emulsification of the 6 formulations was carried out with a commercial homogenizer (PRO250) from Proscientific, Inc., using a ¾ horsepower motor that drove a 30 mm rotor-stator generator, by combining all of the reactants into one vessel and raising the temperature to approximately 90° C. Table 2 provides the formulations and the compositions (in grams) for the 6 test formulations utilizing Tween-80 as the sole surfactant,

TABLE 2

| | formulae | | | | | |
|---|---|---|---|---|---|---|
| | C1 | C1 | C3 | C3 | C5 | C6 |
| D-15 | 2.07 | 2.07 | 2.02 | 2.02 | 2.02 | 2.03 |
| D-35 | 5.17 | 5.17 | 5.04 | 5.04 | 5.05 | 5.07 |
| Polysorbate-80 | 0.20 | 0.20 | 1.00 | 1.00 | 1.50 | 1.51 |
| NaCl | 0.67 | 0.67 | 0.67 | 0.67 | 0.67 | 0.67 |
| $Na_2HPO_4$(anh.) | 0.05 | 0.05 | 0.05 | 0.05 | 0.05 | 0.05 |
| $NaH_2PO_4 2H_2O$ | 0.02 | 0.02 | 0.02 | 0.02 | 0.02 | 0.03 |

TABLE 2-continued

| | formulae | | | | | |
|---|---|---|---|---|---|---|
| | C1 | C1 | C3 | C3 | C5 | C6 |
| EDTA | 0.02 | 0.02 | 0.02 | 0.02 | 0.02 | 0.00 |
| Water | 100 | 100 | 100 | 100 | 100 | 100 |

Footnotes
1. Drakeol refers to a series of NF mineral oils available from Penreco Co. of Butler, PA. The numeral following the letters represents the average molecular weight of the oil, and is an indication of the viscosity of the fluid
2. Polysorbate-80 is a stearyl ether of a polysorbate and is sold under the tradename Tween-80 by ICI (now known as Uniqema, New Castle, DE) in Wilmington, DE.

Results

The six emulsions prepared using Polysorbate-80 as a sole primary surfactant were found to meet the first criterion of providing appropriate separation of the oil and aqueous phases upon resting in the container for several minutes. The second criterion of reconstitution by simple product agitation was also met. However, these formulae failed to meet the third criterion because all were destabilized (as evidenced by surface oil film formation) when agitated for short periods of time on the laboratory shaker or when autoclaved for 30 minutes at 121° C. Increased Polysorbate-80 content in the formulae to 1.50 decreased oil droplet instability, but still failed to meet the third criterion. The failure to meet the third criterion was confirmed in post autoclaved and post shaken samples, in that that the surface oil film formed by droplet coalescence prevented the reconstitution of the emulsion by simple shaking as required by the second criterion.

These formulae thus did not meet the requirements for the desired eye treatment solution. It was found that when using only Polysorbate-80 as a sole primary surfactant, a higher concentration of Polysorbate-80 was required with the following undesirable results: (1) the emulsion was not autoclave stable, (2) the higher concentration of the Polysorbate-80 led to stinging on the eye and (3) the higher concentration of the Polysorbate-80 degraded the performance of the meta stable emulsion on the eye. Thus, the performance of these samples failed by a wide margin to meet the criterion of maintaining the original emulsion characteristics after agitation for a period of time. Therefore, the use of Polysorbate-80 as a sole surfactant for the non-polar oil formula was judged inadequate and was not evaluated clinically.

EXAMPLE 3

Though this example does not illustrate the formation of an emulsion, it does illustrate the basis for rejection of a primary surfactant that would otherwise appear to be suitable for formation of an oil in water emulsion.

The example describes the evaluation of Span 20, a highly viscous water insoluble sorbitan monolaurate, for suitability as a surfactant system for use on the eye. The HLB of 8.6 of this surfactant, and its reported use in ophthalmic products suggested that it would be a suitable surfactant for formation of an oil in water emulsion using mineral oil.

Five concentrations of Span 20, from 0.05% to 1.00% WV were prepared in a buffered normal saline vehicle for evaluation of comfort on the eye. The vehicle used for all formulations was Unisol 4, a buffered saline solution marketed by Alcon Laboratories, Fort Worth, Tex. Unisol 4 had previously been studied and found to be the most comfortable normal saline product for use on the ocular surface. It was therefore used as a vehicle for the test formulations, and was also used as a control.

A drop of each of the 5 test formulations was placed on to the ocular surfaces of each subject, utilizing a 15 ml dropper container that delivered a drop of 40 µl to the ocular surface. The subject was asked to describe the sensation as one of: pleasant, neutral, slight sting, moderate sting, or severe sting.

Results

The results obtained with 6 subjects, all of whom evaluated each of the test formulation on two different days are summarized in Table 3.

TABLE 3

| Formulation | Results |
| --- | --- |
| S477 (Control, Unisol 4) | Pleasant to neutral |
| S478 (0.05% Span 20) | Neutral to slight sting |
| S479 (0.10% Span 20) | Neutral to slight sting |
| S480 (0.20% Span 20) | Slight to moderate sting |
| S481 (0.40% Span 20) | Moderate sting |
| S482 (1.00% Span 20) | Moderate to severe sting |

Footnote
1. Span 20 is a highly viscous water insoluble sorbitan monolaurate sold under the tradename Span 20 by ICI (now known as Uniqema, New Castle, DE) in Wilmington, DE.

In view of the sting when applied to the eye and ocular surfaces, even in concentrations≤0.10%, the use of Span 20 was rejected as a suitable surfactant for an eye treatment composition.

EXAMPLE 4

This example illustrates that Polysorbate-80 found unsatisfactory for purposes of this invention in Example 2 can be made suitable by combination with a secondary surfactant, in this case Octoxynol-40.

The example determines the optimum ratio of a mixed surfactant system comprising Polysorbate-80 as a primary and Octoxynol-40 as a secondary surfactant to maximize the stability of the oil/water interface in the ocular emulsion systems. Formulae utilizing 2.4% Drakeol-15 and 4.8% Drakeol-35 with both Octoxynol-40 and Polysorbate-80 were evaluated at different concentrations. Octoxynol-40 has an HLB of 19 and Polysorbate-80 has an HLB of 15. The two surfactants combined will yield an arithmetic HLB above the HLB believed suitable for formation of a stable oil in water emulsion. The samples were made both with and without disodium EDTA, keeping the concentrations of the other additives at the levels required for eye treatment compositions. The emulsification of the four formulations prepared was carried out with a commercial homogenizer (PRO250) from Proscientific, Inc., using a ¾ horsepower motor which drove a 30 mm rotor-stator generator, by combining all of the reactants into one vessel and raising the temperature to approximately 60° C. Table 4 sets forth the formulations and the compositions (in grams) for the 4 test formulations utilizing the Octoxynol-40 and Polysorbate-80 surfactant systems.

TABLE 4

| Formulae | D1(AD1) | D2(AD2) | D3(AD3) | D4(AD4) |
| --- | --- | --- | --- | --- |
| D-15 | 2.42 | 2.51 | 2.41 | 2.31 |
| D-35 | 4.83 | 4.85 | 4.86 | 4.84 |
| Octoxynol-40 | 1.12 | 1.12 | 0.63 | 0.63 |
| Polysorbate-80 | 0.38 | 0.38 | 0.90 | 0.91 |
| NaCl | 0.67 | 0.67 | 0.67 | 0.67 |
| $Na_2HPO_4$(anh.) | 0.05 | 0.05 | 0.05 | 0.05 |
| $NaH_2PO_42H_2O$ | 0.03 | 0.02 | 0.02 | 0.03 |
| EDTA | 0 | 0.02 | 0.02 | 0 |
| Water | 100 | 100 | 100 | 100 |

Footnotes
1. Drakeol refers to a series of NF mineral oils available from Penreco Co. of Butler, PA. The numeral following the letters represents the average molecular weight of the oil, and is an indication of the viscosity of the fluid.
2. Octoxynol-40 is polyethylene glycol (40) p-isooctylphenyl ether sold under the tradename Synperonic OP-40 by ICI (now known as Uniqema, New Castle, DE) in Wilmington, DE.
3. Polysorbate-80 is a stearyl ether of a polysorbate sold under the tradename Tween-80 by ICI (now known as Uniqema, New Castle, DE) in Wilmington, DE.

Results

All 4 formulations met the three pre-clinical criteria of proper separation, reconstitution of the emulsion by gentle shaking and maintaining the original emulsion characteristics when agitated for a period of time of at least 72 hours on the laboratory Platform Rocker Shaker by Vari-Mix, or when autoclaved for 30 minutes at 121° C.

Microscopic studies and photographs of the samples before and after autoclaving and shaking demonstrated that the oil droplets were not degraded by being subjected to autoclaving at 121° C., or by shaking on the Platform Rocker Shaker by Vari-Mix for 288 hours.

Since this formulation of non-polar oil with the surfactant system of Octoxynol-40 and Polysorbate-80 satisfied the pre-clinical criteria, formulae D1 and D3 were evaluated clinically and were found to adequately augment and restore the lipid layer thickness. The results of the clinical evaluations of formulations D1 and D4 are given in the following table:

| Patient Number | Formulation | Rating before treatment | Rating after treatment |
| --- | --- | --- | --- |
| 1 | D1 | C | A |
| 2 | D1 | D | B |
| 3 | D1 | D | A |
| 4 | D1 | D | B |
| 5 | D1 | C | A |
| 6 | D1 | C | B |
| 7 | D1 | C | A |
| 8 | D4 | D | B |
| 9 | D4 | D | C |
| 10 | D4 | D | B |
| 11 | D4 | D | A |
| 12 | D4 | C | A |
| 13 | D4 | C | A |
| 14 | D4 | C | A |

The clinical evaluations of patient numbers 1 to 14 indicated that the surfactant system of Octoxynol-40 and Polysorbate-80 were efficacious in forming and restoring a lipid layer of improved characteristics and that both formulations were essentially equally effective. The subjective sensation realized with both formulations was evaluated as comfortable, and without any form of adverse sensation. The studies of example 3 indicated that the addition of the surfactant Octoxynol-40 as a second surfactant in combination with Polysorbate-80 satisfied the criteria for a dry eye treatment composition.

EXAMPLE 5

This study was directed to determining the optimal concentrations of the mixed primary and secondary surfactant system of Polysorbate-80 (Tween-80) and Octoxynol-40 for an optimal dry eye treatment formulation.

Six formulations were prepared. Each was formed using a commercial homogenizer (PRO250) from Proscientific, Inc., using a ¾ horsepower motor which drove a 30 mm rotor-stator generator, by combining all of the reactants into one vessel and raising the temperature to approximately 60° C. Table 5 illustrates 6 formulations, where the concentration of Polysorbate-80 is held constant at 0.40%, while the concentration of Octoxynol-40 is varied at 0.30%, 0.60% and 1.20% surfactant levels. The 0.40% Polysorbate-80 concentration was chosen from the result of prior experiments that established that this concentration, when used with higher levels of Octoxynol-40, met the pre-clinical requirements, while lower concentrations of Polysorbate-80 had resulted in minimal but detectable oil droplet degradation after being subjected to autoclaving at 121° C., or by shaking on the Platform Rocker Shaker by Vari-Mix for periods of time from 3 days to 288 hours. It was also considered desirable to utilize the lowest concentrations of both Polysorbate-80 and Octoxynol-40 for a dry eye treatment composition, while meeting the previously described requirements, since the sensitivity of the ocular surface cells and the immune response of the eye can be expected to increase with increasing concentration to any compound placed on the eye. These phenomena may also be exacerbated in dry eye states, since the surface epithelial cells are frequently compromised by the desiccation and lack of lubrication accompanying dry eye states. Table 5 provides the formulations and the compositions (in grams) for the 6 test formulations:

TABLE 5

|  | \multicolumn{6}{c}{Formulae} |
| --- | --- | --- | --- | --- | --- | --- |
|  | F1 | F2 | G1 | G2 | H1 | H2 |
| Polysorbate-80 | 0.41 | 0.41 | 0.40 | 0.40 | 0.40 | 0.40 |
| Octoxynol-40 | 1.21 | 1.21 | 0.60 | 0.60 | 0.30 | 0.30 |
| EDTA.2H$_2$0 | 0.02 | 0.02 | 0.02 | 0.02 | 0.02 | 0.02 |
| NaHPO$_4$ | 0.05 | 0.05 | 0.05 | 0.05 | 0.05 | 0.05 |
| NaH$_2$PO$_4$.2H$_2$0 | 0.02 | 0.02 | 0.02 | 0.02 | 0.02 | 0.02 |
| NaCl | 0.67 | 0.67 | 0.67 | 0.67 | 0.67 | 0.67 |
| H$_2$0 | 100 | 100 | 100 | 100 | 100 | 100 |
| Drakeol-15 | 2.17 | 2.16 | 2.14 | 2.15 | 2.12 | 2.13 |
| Drakeol-35 | 5.42 | 5.41 | 5.36 | 5.38 | 5.31 | 5.33 |
| P/O | 0.5 | 0.5 | 1.0 | 1.0 | 2.0 | 2.0 |
| rpm | 4050 | 10000 | 4050 | 10000 | 4050 | 10000 |

Footnotes
1. Polysorbate-80 is a stearyl ether of a polysorbate sold under the tradename Tween-80 by ICI (now known as Uniqema, New Castle, DE) in Wilmington, DE.
2. Octoxynol-40 is polyethylene glycol (40) p-isooctylphenyl ether sold under the tradename Synperonic OP-40 by ICI (now known as Uniqema, New Castle, DE) in Wilmington, DE.
3. Drakeol refers to a series of NF mineral oils available from Penreco Co. of Butler, PA. The numeral following the letters represents the average molecular weight of the oil, and is an indication of the viscosity.
4. P/O is the molar ratio of the Polysorbate-80 to Octoxynol-40 components.
5. RPM is the speed of the homogenization unit.

The lowest concentration of 0.30 grams Octoxynol-40 with 0.40 grams Polysorbate-80 was found to optimally satisfy the 3 criteria. The low surfactant concentration is desirable due to the possibility of irritancy of ocular tissue, where the sensitivity to a compound placed on the eye can be expected to increase with increasing concentration.

The invention claimed is:

1. An oil in water emulsion, said emulsion using as emulsifiers a combination consisting essentially of a primary surfactant and a secondary surfactant, said primary surfactant being a means for forming an oil in water meta stable emulsion at a physiological pH of between 6.5 and 7.8 alone or in combination with the secondary surfactant, said meta stable emulsion differentiating into an aqueous phase and an oil phase following application to the surface of the eye within 1 minute or within 5 blinks of the eye, and a secondary surfactant, differing from the primary surfactant and used in combination with the primary surfactant, said secondary surfactant being a physiologically acceptable surfactant at a pH between 6.5 and 7.8 and being a means for maintaining the emulsion stable during autoclaving at temperatures in excess of 75° C. or higher without preventing differentiation of the emulsion when applied to the surface of the eye.

2. The oil in water emulsion of claim 1 further comprising a medication.

3. The emulsion of claim 1 where the concentration of the surfactant combination used to form the emulsion is at least 0.01 weight percent of the total composition.

4. The emulsion of claim 3 where the concentration of the surfactant combination varies between 0.25 and 2.5 percent by weight of the total composition.

5. The emulsion of claim 1 where the concentration of oil is that amount required to add between 1 and 10 μl of oil to the eye.

6. The emulsion of claim 1 where the secondary surfactant has ethylene oxide hydrophilic groups.

7. The emulsion of claim 1 where the secondary surfactant is a member selected from the group consisting of $C_8H_{17}C_6H_4(OCH_2CH_2)_nOH$ where n is between 5 and 70 and $C_9H_{19}C_6H_4(OCH_2CH_2)_pOH$ where p is between 5 and 40, and a polyoxyethylene $C_{12-22}$ alkyl ether.

8. The emulsion of claim 7 where n varies between 30 and 50 and p varies between 15 and 30.

9. An oil in water emulsion that is stable during storage but meta stable when applied to the ocular surface whereby it differentiates into a separate water and oil phase within 1 minute or within 5 blinks of the eye following insertion into the eye, said emulsion using as emulsifiers a combination of physiologically acceptable surfactants of a primary surfactant and a secondary surfactant, said primary surfactant comprising means capable of forming a meta stable emulsion at physiological pH by itself or in combination with a secondary surfactant, and a secondary surfactant, differing from the primary surfactant, and used in combination with the primary surfactant, said secondary surfactant being a polyethoxylate selected from the group consisting of $C_8H_{17}C_6H_4(OCH_2CH_2)_nOH$ where n is between 5 and 70 and $C_9H_{19}C_6H_4(OCH_2CH_2)_pOH$ where p is between 5 and 40, and a polyoxyethylene $C_{12-22}$ alkyl ether.

10. The emulsion of claim 9 where the primary surfactant is a polyoxyethylene ether.

11. The emulsion of claim 9 where the concentration of surfactant combination used to form the emulsion is at least 0.01 weight percent of the total composition.

12. The emulsion of claim 11 where the concentration of the surfactant combination varies between 0.25 and 2.5 percent by weight of the total composition.

13. The emulsion of claim 9 where the concentration of the oil is that amount required to add between 1 and 10 µl of oil to the eye.

14. The emulsion of claim 9 where the primary surfactant, the secondary surfactant, or both is a mixture of surfactants.

15. A method for the formation of a meta stable oil in water emulsion able to withstand temperatures in excess of 75° C. without formation of a separate oil layer, the emulsion having an oil concentration of from 2.5 and 12.5 percent by weight and a maximum surfactant concentration of 2.5 percent by weight, said method comprising the steps of [1] selecting a first surfactant that (a) is approved for use on the ocular surface of the human eye, (b) enables formation of an emulsion having the above component concentration levels at physiological pH and is stable during storage, or capable of being reconstituted by simple shaking; and (c) enables formation of an emulsion which, when applied to the ocular surface, differentiates within a minute or less; [2] selecting a second surfactant that (a) is approved for use on the ocular surface of the eye, (b) is compatible with the remaining components of the emulsion; and (b) enables autoclaving at temperatures required to sterilize the emulsion but does not prevent breaking of the emulsion when applied to the ocular surface; and [3] mixing the components of the emulsion to form the emulsion.

16. The method of claim 15 formulated to differentiate following addition to the eye within the shorter time of 30 seconds or the time required for five blinks of the eye.

17. The method of claim 15 where the concentration of the surfactant combination used to form the emulsion varies between 0.25 and 2.5 percent by weight of the total composition.

18. The method of claim 15 where the concentration of oil is that amount required to add between 1 and 10 µl of oil to the eye.

19. The method of claim 15 where the secondary surfactant is a polyethoxylate.

20. The method of claim 15 where the secondary surfactant is a member selected from the group consisting of $C_8H_{17}C_6H_4(OCH_2CH_2)_nOH$ where n is between 5 and 70 and $C_9H_{19}C_6H_4(OCH_2CH_2)_pOH$ where p is between 5 and 40, and a polyoxyethylene $C_{12-22}$ alkyl ether.

21. The method of claim 20 where n varies between 30 and 50 and p varies between 15 and 30.

22. An oil in water emulsion, said emulsion using as emulsifiers a combination consisting essentially of a primary surfactant and a secondary surfactant, said primary surfactant being a physiologically acceptable polyoxyethylene ether surfactant capable of forming an oil in water meta stable emulsion at a physiological pH of between about 6.5 and 7.8 alone or in combination with the secondary surfactant, said meta stable emulsion differentiating into an aqueous phase and an oil phase following application to the surface of the eye within 1 minute or within 5 blinks of the eye, and a secondary surfactant, differing from the primary surfactant and used in combination with the primary surfactant, said secondary surfactant being a physiologically acceptable surfactant at a pH of between 6.5 and 7.8 and capable of maintaining the emulsion stable during autoclaving at temperatures in excess of 75° C. or higher without preventing differentiation of the emulsion when applied to the surface of the eye, said secondary surfactant being a member selected from the group consisting of a compound having the structure $(OCH_2CH_2)_nOH$ where n is between 5 and 70 and $C_9H_{19}C_6H_4(OCH_2CH_2)_pOH$ where p is between 5 and 40, and a polyoxyethylene $C_{12-22}$ alkyl ether.

23. The emulsion of claim 22 where the concentration of the surfactant combination varies between 0.25 and 2.5 percent by weight of the total composition.

24. The oil in water emulsion of claim 22 further comprising a medication.

* * * * *